United States Patent [19]

Maruta

[11] Patent Number: 5,516,668
[45] Date of Patent: May 14, 1996

[54] METHOD FOR DECREASING SEED STORAGE PROTEINS AND FOR TRANSFORMING PLANTS

[75] Inventor: Yoshiyuki Maruta, Iwata, Japan

[73] Assignees: Japan Tobacco Inc., Tokyo; Rice Breeding Research Laboratories, Sendai, both of Japan

[21] Appl. No.: 142,393

[22] PCT Filed: Mar. 24, 1992

[86] PCT No.: PCT/JP92/00355

§ 371 Date: Nov. 24, 1993

§ 102(e) Date: Nov. 24, 1993

[87] PCT Pub. No.: WO93/18643

PCT Pub. Date: Sep. 30, 1993

[51] Int. Cl.$^6$ .............................. C12N 15/00; A01H 1/04
[52] U.S. Cl. .............. 435/172.3; 800/255; 800/DIG. 57; 435/240.4
[58] Field of Search ..................................... 800/205, 255, 800/DIG. 57; 435/172.3, 240.4, 320.1; 536/23.6, 24.1

[56] References Cited

FOREIGN PATENT DOCUMENTS

| | | |
|---|---|---|
| A70597 | 3/1987 | Australia . |
| 0412006 | 6/1991 | European Pat. Off. . |
| 0185298 | 1/1991 | Japan . |

OTHER PUBLICATIONS

Larkins et al. (1985) J Cell Biochem Suppl. O (9 part C):264.
Smith et al. (1988) Nature 324: 724–726.
Leisy et al. (1989) Plant Mol Biol 14:41–50.
van der Krol et al. (1988) Nature 333:866–869.
Okita et al. (1989) J Biol Chem 264(21):12573–12581.
Okamura et al. (1986) Proc Natl Acad Sci USA 83:8240–8244.
Shimamoto et al. (1989) Nature 338: 274–276.

*Primary Examiner*—Douglas W. Robinson
*Assistant Examiner*—Elizabeth F. McElwain
*Attorney, Agent, or Firm*—Birch, Stewart, Kolasch & Birch

[57] ABSTRACT

A method for decreasing a seed storage protein in seeds by a genetic engineering method and a method for transforming plants are disclosed. In the method of the present invention, a gene which is a template of a mRNA having a nucleotide sequence complementary to the mRNA of the seed storage protein is introduced in a plant; and the gene in seeds of the plant is transcribed to inhibit translation of the mRNA of the seed storage protein, thereby decreasing the seed storage protein in the seeds. In the method for transforming plants according to the present invention, a plant is transformed with a vector containing a glutelin promoter and a foreign gene.

13 Claims, 5 Drawing Sheets

```
         10         20         30         40         50         60
GTTAATCATG GTGTAGGCAA CCCAAATAAA ACACCAAAAT ATGCACAAGG CAGTCTGTTG 70         80         90        100        110        120
TATTCTGTAG TACAGACAAA ACTAAAAGTA ATGAAAGAAG ATGTGGTGTT AGAAAAGGAA 130        140        150        160        170        180
ACAATATCAT GAGTAATGTG TGAGCATTAT GGGACCACGA AATAAAAAGA ACATTTTGAT 190        200        210        220        230        240
GAGTCGTGTA TCCTCGATGA GCCTCAAAAG TTCTCTCACC CCGGATAAGA AACCCTTAAG 250        260        270        280        290        300
CAATGTGCAA AGTTTGCATT CTCCACTGAC ATAATGCAAA ATAAGATATC ATCGATGACA 310        320        330        340        350        360
TAGCAACTCA TGCATCATAT CATGCCTCTC TCAACCTATT CATTCCTACT CATCTACATA 370        380        390        400        410        420
AGTATCTTCA GCTAAATGTT AGAACATAAA CCCATAAGTC ACGTTTGATG AGTATTAGGC 430        440        450        460        470        480
GTGACACATG ACAAATCACA GACTCAAGCA AGATAAAGCA AAATGATGTG TACATAAAAC 490        500        510        520        530        540
TCCAGAGCTA TATGTCATAT TGCAAAAAGA GGAGAGCTTA TAAGACAAGG CATGACTCAC 550        560        570        580        590        600
AAAAATTCAC TTGCCTTTCG TGTCAAAAAG AGGAGGGCTT TACATTATCC ATGTCATATT 610        620        630        640        650        660
GCAAAAGAAA GAGAGAAAGA ACAACACAAT GCTGCGTCAA TTATACATAT CTGTATGTCC 670        680        690        700        710        720
ATCATTATTC ATCCACCTTT CGTGTACCAC ACTTCATATA TCATGAGTCA CTTCATGTCT 730        740        750        760        770        780
GGACATTAAC AAACTCTATC TTAACATTTA GATGCAAGAG CCTTTATCTC ACTATAAATG 790        800        810        820        830        840
CACGATGATT TCTCATTGTT TCTCACAAAA AGCATTCAGT TCATTAGTCC TACAACAAC
```

Fig. 1

```
        10         20         30         40         50         60
GTTAATCATG GTGTAGGCAA CCCAAATAAA ACACCAAAAT ATGCACAAGG CAGTCTGTTG 70         80         90        100        110        120
TATTCTGTAG TACAGACAAA ACTAAAAGTA ATGAAAGAAG ATGTGGTGTT AGAAAAGGAA 130        140        150        160        170        180
ACAATATCAT GAGTAATGTG TGAGCATTAT GGGACCACGA AATAAAAAGA ACATTTTGAT 190        200        210        220        230        240
GAGTCGTGTA TCCTCGATGA GCCTCAAAAG TTCTCTCACC CCGGATAAGA AACCCTTAAG 250        260        270        280        290        300
CAATGTGCAA AGTTTGCATT CTCCACTGAC ATAATGCAAA ATAAGATATC ATCGATGACA 310        320        330        340        350        360
TAGCAACTCA TGCATCATAT CATGCCTCTC TCAACCTATT CATTCCTACT CATCTACATA 370        380        390        400        410        420
AGTATCTTCA GCTAAATGTT AGAACATAAA CCCATAAGTC ACGTTTGATG AGTATTAGGC 430        440        450        460        470        480
GTGACACATG ACAAATCACA GACTCAAGCA AGATAAAGCA AAATGATGTG TACATAAAAC 490        500        510        520        530        540
TCCAGAGCTA TATGTCATAT TGCAAAAAGA GGAGAGCTTA TAAGACAAGG CATGACTCAC 550        560        570        580        590        600
AAAAATTCAC TTGCCTTTCG TGTCAAAAAG AGGAGGGCTT TACATTATCC ATGTCATATT 610        620        630        640        650        660
GCAAAAGAAA GAGAGAAAGA ACAACACAAT GCTGCGTCAA TTATACATAT CTGTATGTCC 670        680        690        700        710        720
ATCATTATTC ATCCACCTTT CGTGTACCAC ACTTCATATA TCATGAGTCA CTTCATGTCT 730        740        750        760        770        780
GGACATTAAC AAACTCTATC TTAACATTTA GATGCAAGAG CCTTTATCTC ACTATAAATG 790        800        810        820        830        840
CACGATGATT TCTCATTGTT TCTCACAAAA AGCATTCAGT TCATTAGTCC TACAACAACA 850        860        870        880        890        900
TGGCATCCAT AAATCGCCCC ATAGTTTTCT TCACAGTTTG CTTGTTCCTC TTGTGCGATG 910        920        930        940        950        960
GCTCCCTAGC CCAGCAGCTA TTAGGCCAGA GCACTAGTCA ATGGCAGAGT TCTCGTCGTG 970        980        990       1000       1010       1020
GAAGTCCGAG AGGATGTAGA TTTGATAGGT TGCAAGCATT TGAGCCAATT CGGAGTGTGA 1030       1040       1050       1060       1070       1080
GGTCTCAAGC TGGCACAACT GAGTTCTTCG ATGTCTCTAA TGAGTTGTTT CAATGTACCG 1090       1100       1110       1120       1130       1140
GAGTATCTGT TGTCCGCCGA GTTATTGAAC CTAGAGGCCT ACTACTACCC CATTACACTA 1150       1160       1170       1180       1190       1200
ATGGTGCATC TCTAGTATAT ATCATCCAAG GTTTGTGTAA CAATTTAAGT GCATAATGAA 1210       1220       1230       1240
TTAATGATTG GCTGCGATAT TTACATTGCT TGTAATTAAC
```

Fig. 2

METHOD FOR DECREASING SEED STORAGE PROTEINS AND FOR TRANSFORMING PLANTS

INDUSTRIAL FIELD

This invention relates to a method for decreasing a seed storage protein, thereby obtaining seeds with reduced amount of the protein. This invention also relates to a method for transforming plants.

PRIOR ART

In seeds of higher plants, proteins are contained in an amount of 20–30% by weight in case of beans, and in an amount of about 10% by weight in case of cereals, based on dry weight. Among the proteins in seeds, 70–80% by weight are storage proteins. Particularly, in rice seeds, about 80% by weight of the seed storage proteins is glutelin which is only soluble in dilute acids and dilute alkalis. The remainders are prolamin (10–15% by weight) soluble in organic solvents and globulin (5–10% by weight) solublilized by salts.

Seed storage proteins are important as a protein source in foods, so that they have been well studied from the view points of nutrition and protein chemistry. As a result, in cereals, storage protein genes of maize, wheat, barley and the like have been cloned, amino acid sequences of the proteins have been deduced from the nucleotide sequence, and regulatory regions of the genes have been analyzed.

The cDNA of glutelin which is a seed storage protein in rice has been cloned and complete primary structure of the protein has been determined by sequencing the cDNA. The gene of this protein has been isolated by using the cDNA as a probe (Japanese Laid-open Patent Application (Kokai) No. 63-91085).

In order to clarify the function of the 5' region (glutelin promoter region) of the gene fragment originated from nucleus, a fused gene comprising the glutelin promoter and chloramphenicol acetyltransferase (CAT) gene as a reporter gene was introduced to tobacco plants using Agrobacterium. CAT assay of these transformed tobacco plants revealed that rice glutelin promoter is expressed specifically in endosperm in seeds and is expressed specifically in maturation phase of seeds (Okita et al., Plant Molecular Biology, 14, 41–50 (1989).

For rice grains to be processed, it is demanded that protein content be small. In case of rice used for preparing fermented alcoholic beverage, this is attained by well refining the rice, thereby removing the proteins in the peripheral portion of endosperm which contains proteins in large amounts. In producing rice starch, in order to promote the purity, proteins are removed by treatments with alkalis, surfactants and ultrasonication.

Protein contents in rice grains also influence the taste of the rice. Rice grains with good taste have low contents of proteins. Rice varieties with low contents of proteins have been developed by the conventional cross-breeding or by mutation-breeding.

By virtue of the developments of plant tissue culture techniques and of techniques for introduction of genes, production of transformed plants have been reported. As for plants belonging to the family Gramineae, introduction of a foreign gene by treating protoplasts isolated from cultured cells with polyethylene glycol (Japanese Laid-open Patent Application (Kokai) No. 63-287485; and introduction of a foreign gene by applying electric pulses (Japanese Laid-open Patent Application (Kokai) No. 1-181791) have been reported.

As the promoter for expressing a foreign gene in transformed rice plants, in many cases, 35S promoter of cauliflower mosaic virus (CaMV) is used.

It is known that the function of an RNA such as a mRNA carrying the information of protein synthesis is suppressed by an RNA which has a nucleotide sequence complementary to the aforementioned RNA. Such an RNA is collectively referred to as antisense RNA. Researches for artificially producing antisense RNAs by employing gene recombination techniques are now being made.

For example, a petunia having a color different from that of wild type petunia has been provided by preparing a transformed petunia which produces an antisense RNA of chalcone synthetase concerning the synthesis of flower pigments (European Patent Publication No. 341,885). Further, tomato fruits having longer shelf life than wild type tomatoes have been prepared by suppressing the polygalacturonase which plays an important role to softening of tomato fruits by antisense RNA (European Patent Publication 891,115).

However, no case has been reported in which the antisense RNA technique is applied to the reduction of the seed storage proteins.

Germ and bran of rice grains contain much proteins, lipids, ash and vitamins. These substances accelerate the growth of koji and yeasts to destroy the balance of quality of fermented alcoholic beverage, and the substances are contained in the fermented alcoholic beverage as coloring components and as components giving another taste, thereby deteriorating the quality of the alcoholic beverage. Thus, by refining the rice grains, these undesirable components are eliminated. With the increase in the degree of the refining, the contents of the lipids, ash and globulin which are mainly contained in bran are largely decreased, while the percentages of glutelin and prolamin which are storage proteins in rice grains are increased because they are also contained in endosperm.

Breeding of rice varieties for fermented alcoholic beverage is now carried out aiming at early maturity and short culm. However, in general, in varieties which mature early and have shorter culm, protein contents are high, so that it is very difficult to breed a rice variety which matures earlier and has short culm but has low protein content by a conventional technique. Further, with the method utilizing the induction of mutations, it is necessary to treat a large number of plants, and it takes much labor and time to select the plant with low protein content from the large number of plants.

Further, in cases where the qualities of the seed storage proteins are to be improved, it is necessary to specifically and effectively decrease the storage proteins now contained.

Conventionally, 35S promoter of CaMV is usually used for expressing foreign genes.

However, in transformants of rice, the promoter activity of CaMV 35S promoter is low, especially in endosperm in which the glutelin gene expresses (Shimamoto et al., Mol. Gen. Genet. 220:389–392 (1990)). Therefore, efficient reduction of glutelin protein cannot be expected as long as CaMV 35S promoter is used as a promoter for synthesizing antisense RNA of glutelin.

DISCLOSURE OF THE INVENTION

An object of the present invention is to provide a method for decreasing the amounts of storage proteins in seeds, which is easier and more reliable than the conventional cross-breeding method and the mutation-breeding method.

Another objectof the present invention is to provide a method for transforming plants, by which high transcriptional activity is exhibited even in the tissues, such as endosperm, in which the activity of the conventional CaMV 35S promoter is low.

The present inventors intensively studied to succeed in introducing into a plant a gene which is a template of an antisense RNA against a seed storage protein, and in transcribing the gene in a seed so as to decrease the amount of the seed storage protein, thereby completing the present invention.

That is, the present invention provides a method for decreasing amount of a seed storage protein comprising introducing into a plant a gene which is a template of a mRNA having a nucleotide sequence complementary to the mRNA of said seed storage protein; and transcribing said gene in seeds of said plant to inhibit translation of said mRNA of said seed storage protein, thereby decreasing said seed storage protein in said seeds. The present invention also provides a method for transforming a plant comprising transforming said plant with a vector containing a glutelin promoter and a foreign gene.

By the present invention, a method for decreasing the amount of a seed storage protein and a seed having reduced content of a storage protein were provided. By the method according to the present invention, the decrease in the seed storage protein can be attained more easily and more reliably than the conventional cross-breeding method and the mutation-breeding method.

Further, by the present invention, a method for transforming plants by which high transcriptional activity is exhibited, and in turn, a foreign gene is effectively expressed even in tissues such as endosperm in which the transcriptional activity of the CaMV 35S promoter conventionally used is low.

BRIEF DESCRIPTION OF THE DRAWINGS

FIG. 1 shows the nucleotide sequence of a promoter of glutelin, SEQ. ID. NO.: 1

FIG. 2 shows the nucleotide sequence of a DNA fragment containing glutelin promoter and glutelin gene, which was cloned in an example of the present invention, SEQ. ID. No.: 2

BEST MODE FOR CARRYING OUT THE INVENTION

Figure 3:
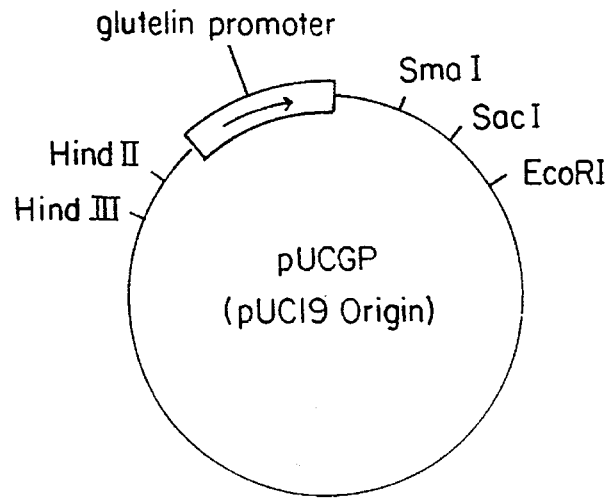
FIG. 3 shows a gene map of a recombinant plasmid vector prepared in an example of the present invention as an intermediate for preparing a recombinant plasmid vector used for transformation.

In the method of the present invention, an antisense RNA against the mRNA of a seed storage protein is produced in a seed so as to inhibit the translation of the mRNA of the seed storage protein.

Examples of the plants to which the method of the present invention is applied include those which bear seeds containing storage proteins, such as rice, wheat, barley and soybean. The glutelin gene has already been cloned and its nucleotide sequence is also known, so that the cloning of this gene from a genomic DNA library of rice can be carried out by a conventional method utilizing the cDNA of glutelin as a probe.

By inserting the glutelin cDNA into a vector plasmid which can replicate in plant cells, and by transforming the plant with the obtained recombinant vector, the antisense RNA against the glutelin mRNA can be produced in the plant. Vector plasmids replicable in plants are well-known in the art. For example, in the example hereinbelow described, commercially available pUC19 (Messing et al., Gene, 33:103–119 (1985); commercially available from PHARMACIA) is used. As will be described in the example below, in order to increase the production of the antisense RNA, two or more glutelin cDNAs may be inserted in the antisense direction in a single vector plasmid. The methods for transforming plant cells per se are also well-known in the art. For example, transformation of plants can be carried out by the electroporation method in which a foreign DNA is introduced into protoplasts by applying electric pulse; or by treating protoplasts with polyethylene glycol.

As described in the section of PRIOR ART, in the conventional transformation of plants, 35S promoter of CaMV is used as the promoter for expressing a foreign gene in the plants. However, 35S promoter of CaMV has low activity in seeds, so that the promoter is not suitable for the reduction of the storage proteins in seeds. The present inventors discovered that the promoter of glutelin has a high activity in seeds and succeeded in the reduction of the seed storage protein using this promoter. This promoter has the nucleotide sequence shown in FIG. 1 and SEQ. I.D. NO.: 1, and is located upstream the structural gene of glutelin.

In carrying out transformation of plant cells, it is convenient if the recombinant vector contains a gene expressing a drug resistance (in the example described below, hygromycin-resistant gene is used) in addition to the glutelin cDNA inserted in the antisense direction and the glutelin promoter. Since such a marker gene is necessary only in the selection of the transformed cells and is no longer necessary after the selection, it is preferred to insert the marker gene into a recombinant vector other than the above-described recombinant vector containing the glutelin cDNA. The promoter of the marker gene in such a vector is not necessary to be the glutelin promoter, but may be 35S promoter of CaMV conventionally used.

By regenerating the transformed protoplasts thus obtained, culturing the same to regenerate plants, and by selecting the antisense gene of glutelin by examining the DNAs in the transformants by Southern hybridization, a seed in which the amount of the seed storage protein is decreased and a plant bearing such a seed can be obtained.

Although the above-mentioned method is for reducing glutelin which is a major seed storage protein, the above-described method can be applied for decreasing seed storage proteins other than glutelin, and the glutelin promoter can be utilized for the reduction of seed storage proteins other than glutelin.

Further, glutelin promoter has never been used for transformation of plants. Thus, the present invention first provided a method for transforming plants with a vector containing the glutelin promoter and a foreign gene. The method for transformation of plants according to the present invention can be applied not only to the method for decreasing the amount of a seed storage protein, but can be applied to a method for expressing a desired foreign gene in seeds or in other tissues.

The present invention will now be described by way of an example thereof. However, the present invention is not limited to the following example.

EXAMPLE

In the following example, molecular operations were carried out in accordance with Maniatis et al., Molecular Cloning, Cold Spring Harbor (1982) unless otherwise specified.

(1) Cloning of Nuclear DNA Encoding Rice Glutelin and Isolation of Fragment Containing Promoter Region of Glutelin Gene (FIG. 3)

From green leaves of rice cultivar Sasanishiki, nuclear DNAs were extracted according to a conventional method (Plant Gene Technology Manual: published by KODAN-SHA). The nuclear DNAs were treated with BamHI and the resulting fragments were inserted into the BamHI site of EMBL3 phage (commercially available from Stratagene). A genomic library was prepared from the resultant by the in vitro packaging method.

From the obtained genomic library, recombinant phages containing a gene corresponding to glutelin gene were selected by using glutelin cDNA as a probe. The fragments containing the gene corresponding to the glutelin gene were isolated and purified, and the nucleotide sequence of the gene was determined according to the Sanger method (Proc. Natl. Acad. Sci. USA, 74:5463 (1979)), the determined nucleotide sequence being shown in FIG. 2 and SEQ. I.D. NO.: 2

Based on the determined nucleotide sequence, a fragment containing promoter region of glutelin was cut out with restriction enzymes BamHI and SpeI, and 3' end thereof was sequentially cut off by exonuclease III (commercially available from TAKARA SHUZO) to prepare a fragment containing only the promoter region of glutelin. To the 3' end of the resulting fragment, a BamHI linker was attached and the resulting fragment was subcloned into the BamHI site of the plasmid pUC19 (supra) to obtain a plasmid pUCGP (FIG. 3).

Figure 4:
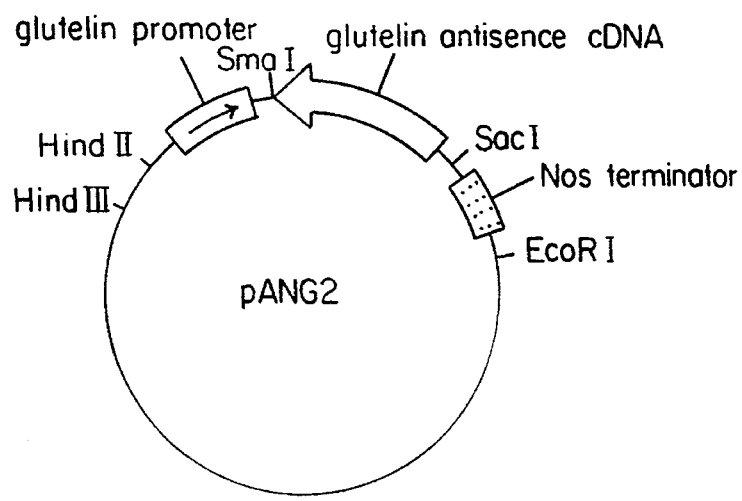
FIGS. 4 and 5 show gene maps of recombinant plasmid vectors which were used for transformation in an example of the present invention.
Figure 5:
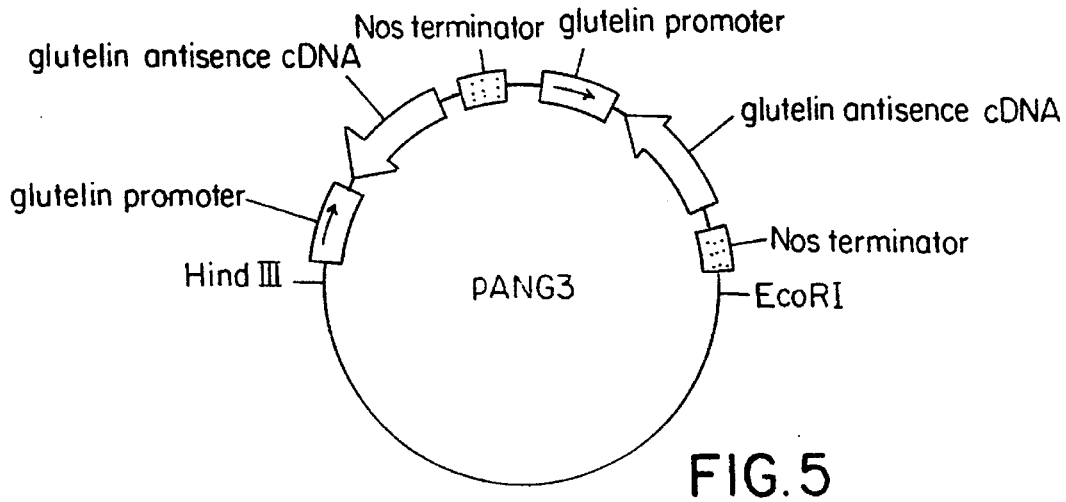

(2) Construction of Vector by Which Glutelin Antisense RNA Can Be Transcribed (FIGS. 4 and 5)

Glutelin cDNA having the complete length was inserted in the antisense direction into SmaI-SacI site downstream the glutelin promoter region in the above-described plasmid pUCGP. Further, Nos (Nopaline synthase) terminator (Goodman et al., Journal of Molecular and Applied Genetics: 561–573 (1982)) was inserted into SacI-EcoRI site downstream the antisense glutelin cDNA sequence to obtain a plasmid pANG2 containing an antisense gene of glutelin (FIG. 4).

The fragment containing the glutelin promoter, antisense glutelin cDNA and Nos terminator was cut out by treating the vector with EcoRI and HindIII and the EcoRI end of the fragment was filled in by treatment with Klenow fragment. The resulting fragment was inserted into HindIII-HincII site of plasmid pANG2 and the resultant was cyclized to obtain a plasmid pANG3 containing two glutelin antisense genes arranged in series (FIG. 5).

(3) Transformation of Rice Plants

From plants of rice cultivars Nipponbare and Akihikari cultivated in a green house, anthers were collected and sterilized with ethanol and aqueous sodium hypochlorite solution. The resulting anthers were cultured in AAmedium (Muller et al., Mol. Gen. Genet. 161:67–76 (1987); 1 ppm of 2,4-D, 0.2 ppm of kinetin, 0.1 ppm of gibberellin) at 25° C. under shaking at 120 rpm in the dark to obtain suspension cultures.

The suspension cultures on Day 4 from subculture were treated with an enzyme solution containing 1 wt % of Cellulase RS, 1 wt % of Macerozyme R-10, 0.1 wt % of Pectolyase Y-23, 0.5 wt % of Driselase and 0.4M mannitol, pH 5.8, at 30° C. for 2 hours to obtain protoplasts.

The obtained protoplasts were suspended in a buffer containing 0.1 wt % of MES, 70 mM KCl, 5 mMMgCl$_2$ and 0.4M mannitol, pH 5.8.

To this suspension of protoplasts, 50 µg/ml of a plasmid containing CaMV 35S promoter as a promoter, a hygromycinphosphotransferase gene as a foreign gene, and a terminator originated from CaMV; and 50 µg/ml of plasmid pANG2 or pANG3 containing glutelin antisense gene were added, and the resulting suspension of protoplasts was cooled in ice for 5 minutes. The resultant was then transferred to a plastic cell and direct current pulses were applied thereto employing a capacitor having a capacitance of 250 µF, 625 V/cm of electric voltage and 400 Ω of resistance.

After applying the pulses, the resulting suspension of protoplasts was cooled in ice for 20 minutes and the protoplasts were cultured in R2 protoplast liquid medium (Ohira et al., Plant Cell Physiol. 14:1113–1121 (1973)) at 25° C. under illumination.

After culturing the protoplasts in R2 medium for 1–2 months, the cells were placed on a solid medium based on N6 medium (Chu et al., Scientia Scinica 18:659–663 (1975)) containing 20 µg/ml of hygromycin and hygromycin-resistant colonies were selected.

One month later, the hygromycin-resistant colonies were placed on a regeneration solid medium based on N6 medium and cultured for 1–2 months under illumination. During this culture, shoots and roots emerged and the colonies were grown into infant plants.

The infant plants were transferred to pots and cultivated. As a result, 23 fertile rice plants were obtained for Nipponbare and 10 fertile rice plants were obtained for Akihikari.

(4) Confirmation of Transformation

From green leaves of the plants obtained in (3), DNAs were extracted and examined for the existence of the introduced gene by Southern hybridization.

As a result, among 23 plants of Nipponbare, 20 plants retained hygromycinphosphotransferase gene, and among these, 5 plants also retained glutelin antisense gene.

Among 10 plants of Akihikari, 4 plants retained hygromycinphosphotransferase gene, and among these, 2 plants also retained glutelin antisense gene.

(5) Analysis of Seeds of Transformed Rice Plants

The plants which were confirmed to retain the glutelin antisense gene were cultivated until they bore seeds and completely maturated seeds were collected therefrom.

After pulverizing the seeds one by one in a mortar, the resultant was suspended in a buffer containing 4 wt % SDS and 6M of urea. The resulting suspension was centrifuged and the supernatant was subjected to 16 wt % polyacrylamide gel electrophoresis, followed by staining the gel with Coomassie Blue. The gel after staining was applied to a densitometer and the degree of staining with Coomassie Blue of each rice grain was converted into a numerical value so as to calculate the glutelin content of each grain.

As a control, the glutelin contents of Nipponbare and Akihikari which were not transformed were also calculated.

Figure 6:
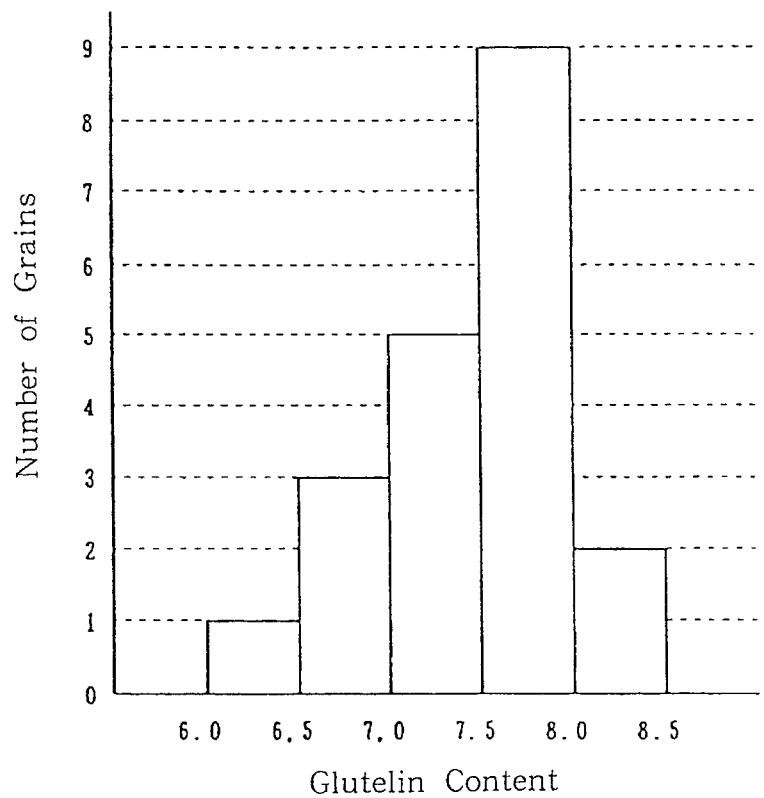
FIGS. 6 and 8 are histograms showing glutelin contents (ratio to globulin) of 20 control rice grains.
Figure 7:
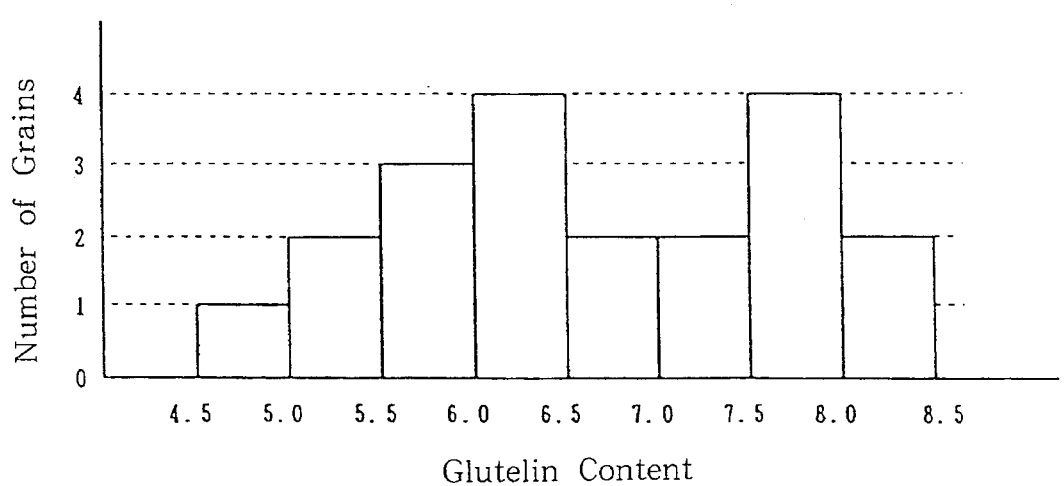
FIGS. 7 and 9 are histograms showing glutelin contents (ratio to globulin) of 20 rice grains obtained by the method of the present invention.
Figure 8:
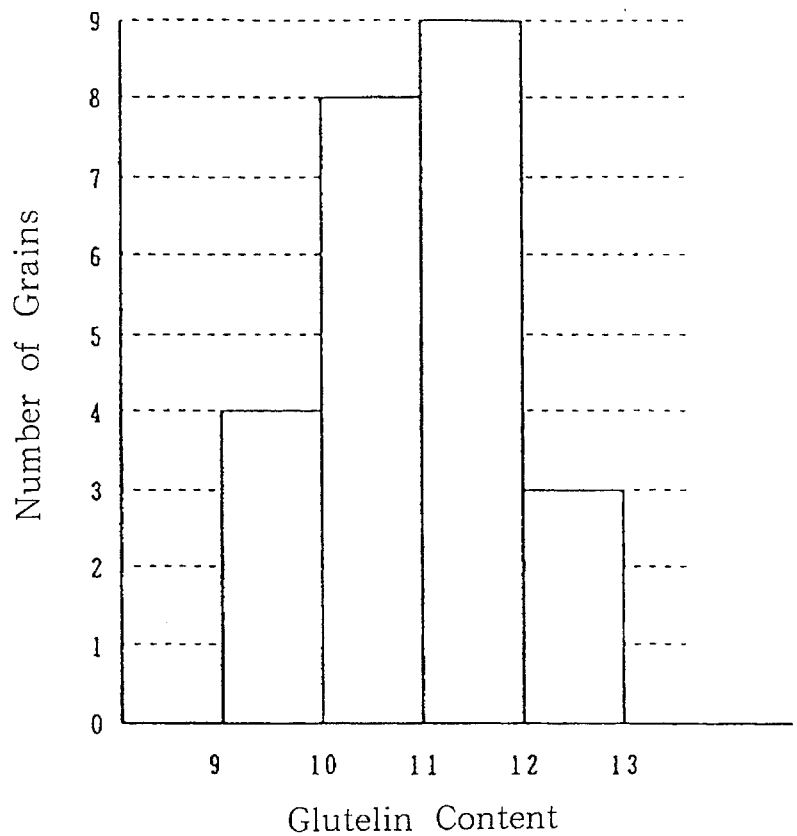
Figure 9:
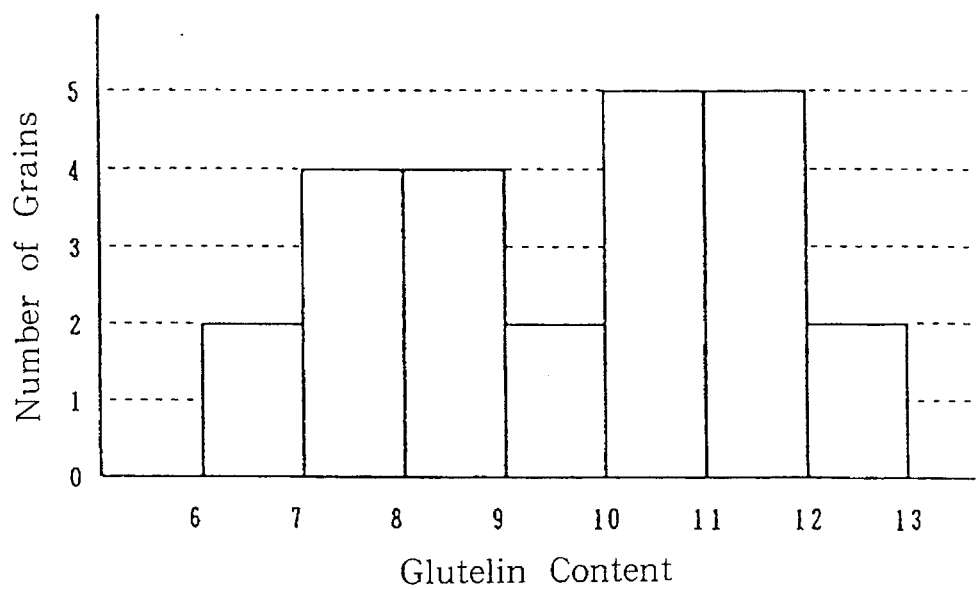

The results are shown in FIGS. 6 to 9. FIG. 6 shows the results of control Nipponbare, FIG. 7 shows the results of Nipponbare transformed by the method of the present invention, FIG. 8 shows the results of control Akihikari and FIG. 9 shows the results of Akihikari transformed by the method of the present invention. These figures show the analytical results of randomly selected 20 rice grains, respectively, in terms of histograms. The glutelin contents are expressed in terms of indices taking the content of the 26 kDa globulin in a single grain as 1.

In the 20 Nipponbare grains, 10 grains exhibited values lower than 95% reliable range (6.5–8.42) in the distribution of the glutelin contents of control Nipponbare grains. Since this decrease in glutelin content cannot be caused by an environmental change, the reduction of the glutelin content by the glutelin antisense gene is clear.

As is apparent from the histograms of the transformants, the glutelin contents vary in the seeds obtained from the plants of the present generation in which the glutelin antisense gene was introduced. This is because of the $F_2$-like segregation of the seeds according to Mendel's heredity.

Thus, from transformed Nipponbare grains, 5 grains in which the decrease in the glutelin content is not observed and 5 grains in which the decrease in the glutelin content is prominent were selected and the glutelin content and globulin content were determined under more precise conditions. The results are shown in Tables 1 and 2.

TABLE 1

Rice Grains in Which Decrease in Glutelin is Prominent (Transformants)

| Rice Grain No. | Globulin Content (%) | Glutelin Content (%) | Glu/Glo* |
|---|---|---|---|
| Nipponbare 1 | 12.7 | 63.9 | 5.03 |
| Nipponbare 2 | 13.8 | 70.4 | 5.10 |
| Nipponbare 3 | 11.5 | 60.5 | 5.26 |
| Nipponbare 4 | 12.8 | 61.7 | 4.82 |
| Nipponbare 5 | 11.2 | 56.6 | 5.05 |
| Average | 12.4 | 62.6 | 5.05 |

*glutelin/globulin

TABLE 2

Rice Grains in Which Decrease in Glutelin is not Observed (Transformants)

| Rice Grain No. | Globulin Content (%) | Glutelin Content (%) | Glu/Glo* |
|---|---|---|---|
| Nipponbare 6 | 12.1 | 76.5 | 6.32 |
| Nipponbare 7 | 12.0 | 80.7 | 6.73 |
| Nipponbare 8 | 11.8 | 80.5 | 6.82 |
| Nipponbare 9 | 12.6 | 75.7 | 6.01 |
| Nipponbare 10 | 11.3 | 80.9 | 7.16 |
| Average | 12.0 | 78.9 | 6.61 |

*glutelin/globulin

In the 24 Akihikari grains, 10 grains exhibited values lower than 95% reliable range (9.14–13.02) in the distribution of the glutelin contents of control Nipponbare grains. Thus, similarly, the decrease in the glutelin content by the glutelin antisense gene is clear in Akihikari.

Further, similar to transformed Nipponbare, 5 grains in which the decrease in the glutelin content is not observed and 5 grains in which the decrease in the glutelin content is prominent were selected and the analysis was carried out under more precise conditions. The results are shown in Tables 3 and 4.

TABLE 3

Rice Grains in Which Decrease in Glutelin is Prominent (Transformants)

| Rice Grain No. | Globulin Content (%) | Glutelin Content (%) | Glu/Glo* |
|---|---|---|---|
| Akihikari 1 | 11.6 | 59.9 | 5.16 |
| Akihikari 2 | 11.7 | 60.7 | 5.19 |
| Akihikari 3 | 10.2 | 56.1 | 5.50 |
| Akihikari 4 | 11.6 | 58.7 | 5.06 |
| Akihikari 5 | 10.9 | 62.8 | 5.76 |
| Average | 11.2 | 59.6 | 5.33 |

*glutelin/globulin

TABLE 4

Rice Grains in Which Decrease in Glutelin is not Observed (Transformants)

| Rice Grain No. | Globulin Content (%) | Glutelin Content (%) | Glu/Glo* |
|---|---|---|---|
| Akihikari 6 | 8.9 | 69.3 | 7.79 |
| Akihikari 7 | 8.7 | 71.9 | 8.26 |
| Akihikari 8 | 8.0 | 70.8 | 8.85 |
| Akihikari 9 | 8.0 | 63.1 | 7.89 |
| Akihikari 10 | 8.3 | 67.0 | 8.07 |
| Average | 8.4 | 68.4 | 8.17 |

*glutelin/globulin

I claim:

1. A method for decreasing the amount of glutelin in plant seeds, comprising:

introducing into a rice plant a gene which is a template for the transcription of an antisense RNA against glutelin; and transcribing said gene in seeds from said rice plant to inhibit translation of mRNA of glutelin, thereby decreasing the amount of glutelin in said seeds in comparison to the amount of glutelin contained in seeds from said rice plant into which said gene has not been introduced.

2. The method according to claim 1, wherein the transcription of said gene is carried out utilizing a promoter of a glutelin gene.

3. The method according to claim 2 which is carried out by transforming said plant with pANG2 or pANG3.

4. A transformed seed which is prepared by the method according to claim 1, which has decreased glutelin relative to the amount of glutelin in a corresponding rice seed which is the same as said transformed rice seed except that it has not been transformed by said method.

5. The method according to claim 1, further comprising introducing into said rice plant two copies of said gene.

6. The method according to claim 1, wherein said rice plant is rice cultivar Nipponbare or Akihikari.

7. A method for decreasing the amount of glutelin in rice seeds, comprising:

introducing into a rice plant a glutelin gene which acts as a template for the transcription of an antisense RNA against glutelin by transforming said rice plant with plasmid pANG2 or plasmid pANG3, and transcribing said glutelin gene in seeds of said rice plant utilizing a glutelin gene promoter to inhibit translation of mRNA of said glutelin, thereby decreasing the amount of said glutelin in said seeds in comparison to the amount of said glutelin contained in seeds of said rice plant into which said glutelin gene has not been introduced.

8. The method according to claim 7, wherein said rice plant is rice cultivar Nipponbare or Akihikari.

9. A rice seed having a decreased amount of glutelin, which is prepared by the method of claim 7.

10. The transformed rice seed according to claim 4, wherein the transcription of said gene is carried out utilizing a promoter of a glutelin gene.

11. The transformed rice seed according to claim 10, which is carried out by transforming said plant with pANG2 or pANG3.

12. The transformed rice seed according to claim 4, which is prepared by introducing into said plant two copies of said gene.

13. The transformed rice seed according to claim 4, wherein said rice cultivar is Nipponbare or Akihikari.

\* \* \* \* \*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 839 base pairs
        ( B ) TYPE: nucleic acid (C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Oryza sativa (xi) SEQUENCE DESCRIPTION: SEQ ID NO:1:

| | | | | | | |
|---|---|---|---|---|---|---|
| GTTAATCATG | GTGTAGGCAA | CCCAAATAAA | ACACCAAAAT | ATGCACAAGG | CAGTCTGTTG | 60 |
| TATTCTGTAG | TACAGACAAA | ACTAAAGTA | ATGAAAGAAG | ATGTGGTGTT | AGAAAAGGAA | 120 |
| ACAATATCAT | GAGTAATGTG | TGAGCATTAT | GGGACCACGA | AATAAAAAGA | ACATTTTGAT | 180 |
| GAGTCGTGTA | TCCTCGATGA | GCCTCAAAAG | TTCTCTCACC | CCGGATAAGA | AACCCTTAAG | 240 |
| CAATGTGCAA | AGTTTGCATT | CTCCACTGAC | ATAATGCAAA | ATAAGATATC | ATCGATGACA | 300 |
| TAGCAACTCA | TGCATCATAT | CATGCCTCTC | TCAACCTATT | CATTCCTACT | CATCTACATA | 360 |
| AGTATCTTCA | GCTAAATGTT | AGAACATAAA | CCCATAAGTC | ACGTTTGATG | AGTATTAGGC | 420 |
| GTGACACATG | ACAAATCACA | GACTCAAGCA | AGATAAAGCA | AAATGATGTG | TACATAAAAC | 480 |
| TCCAGAGCTA | TATGTCATAT | TGCAAAAAGA | GGAGAGCTTA | TAAGACAAGG | CATGACTCAC | 540 |
| AAAAATTCAC | TTGCCTTTCG | TGTCAAAAAG | AGGAGGGCTT | TACATTATCC | ATGTCATATT | 600 |
| GCAAAGAAA | GAGAGAAAGA | ACAACACAAT | GCTGCGTCAA | TTATACATAT | CTGTATGTCC | 660 |
| ATCATTATTC | ATCCACCTTT | CGTGTACCAC | ACTTCATATA | TCATGAGTCA | CTTCATGTCT | 720 |
| GGACATTAAC | AAACTCTATC | TTAACATTTA | GATGCAAGAG | CCTTTATCTC | ACTATAAATG | 780 |
| CACGATGATT | TCTCATTGTT | TCTCACAAAA | AGCATTCAGT | TCATTAGTCC | TACAACAAC | 839 |

(2) INFORMATION FOR SEQ ID NO:2:

(i) SEQUENCE CHARACTERISTICS:
    (A) LENGTH: 1240 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Oryza sativa (xi) SEQUENCE DESCRIPTION: SEQ ID NO:2:

| | | | | | | |
|---|---|---|---|---|---|---|
| GTTAATCATG | GTGTAGGCAA | CCCAAATAAA | ACACCAAAAT | ATGCACAAGG | CAGTCTGTTG | 60 |
| TATTCTGTAG | TACAGACAAA | ACTAAAGTA | ATGAAAGAAG | ATGTGGTGTT | AGAAAAGGAA | 120 |
| ACAATATCAT | GAGTAATGTG | TGAGCATTAT | GGGACCACGA | AATAAAAAGA | ACATTTTGAT | 180 |
| GAGTCGTGTA | TCCTCGATGA | GCCTCAAAAG | TTCTCTCACC | CCGGATAAGA | AACCCTTAAG | 240 |
| CAATGTGCAA | AGTTTGCATT | CTCCACTGAC | ATAATGCAAA | ATAAGATATC | ATCGATGACA | 300 |
| TAGCAACTCA | TGCATCATAT | CATGCCTCTC | TCAACCTATT | CATTCCTACT | CATCTACATA | 360 |
| AGTATCTTCA | GCTAAATGTT | AGAACATAAA | CCCATAAGTC | ACGTTTGATG | AGTATTAGGC | 420 |
| GTGACACATG | ACAAATCACA | GACTCAAGCA | AGATAAAGCA | AAATGATGTG | TACATAAAAC | 480 |
| TCCAGAGCTA | TATGTCATAT | TGCAAAAAGA | GGAGAGCTTA | TAAGACAAGG | CATGACTCAC | 540 |

| | | | | | | |
|---|---|---|---|---|---|---|
| AAAAATTCAC | TTGCCTTTCG | TGTCAAAAAG | AGGAGGGCTT | TACATTATCC | ATGTCATATT | 600 |
| GCAAAAGAAA | GAGAGAAAGA | ACAACACAAT | GCTGCGTCAA | TTATACATAT | CTGTATGTCC | 660 |
| ATCATTATTC | ATCCACCTTT | CGTGTACCAC | ACTTCATATA | TCATGAGTCA | CTTCATGTCT | 720 |
| GGACATTAAC | AAACTCTATC | TTAACATTTA | GATGCAAGAG | CCTTTATCTC | ACTATAAATG | 780 |
| CACGATGATT | TCTCATTGTT | TCTCACAAAA | AGCATTCAGT | TCATTAGTCC | TACAACAACA | 840 |
| TGGCATCCAT | AAATCGCCCC | ATAGTTTTCT | TCACAGTTTG | CTTGTTCCTC | TTGTGCGATG | 900 |
| GCTCCCTAGC | CCAGCAGCTA | TTAGGCCAGA | GCACTAGTCA | ATGGCAGAGT | TCTCGTCGTG | 960 |
| GAAGTCCGAG | AGGATGTAGA | TTTGATAGGT | TGCAAGCATT | TGAGCCAATT | CGGAGTGTGA | 1020 |
| GGTCTCAAGC | TGGCACAACT | GAGTTCTTCG | ATGTCTCTAA | TGAGTTGTTT | CAATGTACCG | 1080 |
| GAGTATCTGT | TGTCCGCCGA | GTTATTGAAC | CTAGAGGCCT | ACTACTACCC | CATTACACTA | 1140 |
| ATGGTGCATC | TCTAGTATAT | ATCATCCAAG | GTTTGTGTAA | CAATTTAAGT | GCATAATGAA | 1200 |
| TTAATGATTG | GCTGCGATAT | TTACATTGCT | TGTAATTAAC | | | 1240 |